US008894201B2

(12) United States Patent
Pugh et al.

(10) Patent No.: US 8,894,201 B2
(45) Date of Patent: Nov. 25, 2014

(54) METHODS AND OPHTHALMIC DEVICES WITH THIN FILM TRANSISTORS

(71) Applicant: Johnson & Johnson Vision Care, Inc., Jacksonville, FL (US)

(72) Inventors: Randall B. Pugh, Jacksonville, FL (US); Frederick A. Flitsch, New Windsor, NY (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 13/840,791

(22) Filed: Mar. 15, 2013

(65) Prior Publication Data

US 2014/0273316 A1    Sep. 18, 2014

(51) Int. Cl.
G02C 7/08    (2006.01)
H01L 51/00    (2006.01)

(52) U.S. Cl.
CPC ................. *H01L 51/0002* (2013.01)
USPC .......... 351/158; 351/159.39; 438/19

(58) Field of Classification Search
CPC .... H01L 27/14692; B24B 9/142; B24B 9/146
USPC ........................................ 438/19
See application file for complete search history.

(56) References Cited

U.S. PATENT DOCUMENTS

| | | | | |
|---|---|---|---|---|
| 5,491,347 A * | 2/1996 | Allen et al. | ...................... | 257/59 |
| 5,519,524 A * | 5/1996 | Fergason et al. | ............... | 349/149 |
| 7,425,767 B2 * | 9/2008 | Lin | ................................ | 257/781 |
| 8,118,752 B2 * | 2/2012 | Hetling et al. | ................. | 600/558 |
| 8,363,020 B2 * | 1/2013 | Li et al. | ........................... | 345/173 |
| 2005/0285099 A1 | 12/2005 | Bao et al. | | |
| 2008/0111131 A1 * | 5/2008 | Yang | ............................... | 257/40 |
| 2011/0084834 A1 | 4/2011 | Sabeta | | |
| 2012/0245444 A1 | 9/2012 | Otis et al. | | |
| 2013/0215377 A1 * | 8/2013 | Pugh et al. | ............... | 351/159.39 |

FOREIGN PATENT DOCUMENTS

WO    WO 2012118777 A1    9/2012
WO    WO 2012122411 A1    9/2012

OTHER PUBLICATIONS

XP055122710, Retrieved from the Internet: RL:http://web.archive.org/web/20120426153    014/http://en.wikipedia.org/wiki/Organic field-effect transistor—Apr. 26, 2012 [retrieved on Jun. 11, 2014].
European Search Report for Application No. Ep 14 16 0027 Date of Completion of Report Jun. 12 2014.

* cited by examiner

*Primary Examiner* — Zandra Smith
*Assistant Examiner* — Damian A Hillman

(57) ABSTRACT

This invention discloses methods and apparatus to form organic semiconductor transistors upon three-dimensionally formed insert devices. In some embodiments, the present invention includes incorporating the three-dimensional surfaces with organic semiconductor-based thin film transistors, electrical interconnects, and energization elements into an insert for incorporation into ophthalmic lenses. In some embodiments, the formed insert may be directly used as an ophthalmic device or incorporated into an ophthalmic device.

13 Claims, 9 Drawing Sheets

500

| Step | Description |
|---|---|
| 501 | CLEAN THE SURFACE OF A FLAT SUBSTRATE |
| 502 | DEPOSIT GATE METAL FEATURES |
| 503 | DEPOSIT DIELECTRIC FILM LAYER |
| 504 | DEPOSIT p-TYPE ORGANIC SEMICONDUCTOR LAYER IN SELECTED REGIONS |
| 505 | DEPOSIT n-TYPE ORGANIC SEMICONDUCTOR LAYER IN SELECTED REGIONS |
| 506 | DEPOSIT SOURCE AND DRAIN METALLIC ELECTRODES |
| 507 | DEPOSIT DIELECTRIC INSULATING LAYER |
| 508 | OPEN CONTACT "HOLES" INTO DIELECTRIC INSULATING LAYERS AT LEAST PARTIALLY ABOVE METALLIC ELECTRODES |

FIG. 5

METHODS AND OPHTHALMIC DEVICES WITH THIN FILM TRANSISTORS

FIELD OF USE

This invention describes apparatus and methods to form organic semiconductor transistors on ophthalmic device insert components. In some embodiments, the methods and apparatus to configure organic semiconductor transistors within ophthalmic devices form on surfaces that occur on substrates that have three-dimensional shapes. In some embodiments, a field of use for the methods and apparatus may include ophthalmic devices that incorporate energization elements, inserts, and organic semiconductor devices.

BACKGROUND

Traditionally an ophthalmic device, such as a contact lens, an intraocular lens, or a punctal plug included a biocompatible device with a corrective, cosmetic, or therapeutic quality. A contact lens, for example, may provide one or more of: vision correcting functionality; cosmetic enhancement; and therapeutic effects. Each function is provided by a physical characteristic of the lens. A design incorporating a refractive quality into a lens may provide a vision corrective function. A pigment incorporated into the lens may provide a cosmetic enhancement. An active agent incorporated into a lens may provide a therapeutic functionality. Such physical characteristics are accomplished without the lens entering into an energized state. A punctal plug has traditionally been a passive device.

More recently, it has been theorized that active components may be incorporated into a contact lens. Some components may include semiconductor devices. Some examples have shown semiconductor devices embedded in a contact lens placed upon animal eyes. It has also been described how the active components may be energized and activated in numerous manners within the lens structure itself. The topology and size of the space defined by the lens structure creates a novel and challenging environment for the definition of various functionalities. In many embodiments, it is important to provide reliable, compact, and cost effective means to energize components within an ophthalmic device. In some embodiments, these energization elements may include batteries that may in turn be formed from "alkaline" cell-based chemistry. Connected to these energization elements may be other components that utilize electrical energy. In some embodiments, these other components may include transistors to perform circuit functions. It may also be desirable to include semiconductor devices in such devices organic.

SUMMARY

Accordingly, the present invention includes methods and apparatus to define organic semiconductor transistors upon one or more ophthalmic lens insert surfaces which may contain three-dimensional shapes and which may be inserted into an ophthalmic device. In some embodiments, an ophthalmic lens insert is provided that may be energized and incorporated into an ophthalmic device.

In some embodiments, a method of forming an ophthalmic device comprising depositing an organic semiconductor layer on a substrate, dividing the substrate into insert pieces wherein each insert piece comprises an organic semiconductor, attaching an insert piece onto an ophthalmic lens insert, and forming an encapsulating layer around the ophthalmic lens insert are disclosed In some embodiments, the substrate is silicon wafer. In some embodiments, the encapsulating layer is paralene. In some other embodiments, the encapsulating layer is forming a hydrogel around the lens insert.

In some embodiments, methods of forming at least a first gate conductor on the substrate are disclosed. In some embodiments, additionally methods of depositing an energization element upon the substrate in electrical communication with the first gate conductor are disclosed. In some embodiments, the energization element is an electrochemical cell.

In some embodiments, the organic semiconductor layer comprises an n-type organic semiconductor. In some embodiments, the organic semiconductor layer comprises a p-type organic semiconductor. In some embodiments, the organic semiconductor layer comprises an n-type organic semiconductor, a p-type organic semiconductor, and a combination thereof. In some embodiments, the n-type organic semiconductor layer comprises copper hexadecafluorophthalocyanine ($F_{15}CuPc$). In some embodiments, the p-type organic semiconductor layer comprises pentacene.

In some embodiments, the energization element is comprised of more than one electrochemical cell, the electrochemical cells are connected at least in part in a series manner. In some embodiments, the first gate conductor comprises a transparent electrode. In some embodiments, the transparent electrode comprises indium tin oxide.

In some embodiments, a method of forming an ophthalmic device comprising: attaching a first conductive trace to a thin film transistor, depositing an organic semiconductor layer fixedly attached the thin film transistor onto an ophthalmic insert device, forming an encapsulating layer around the ophthalmic lens insert, and forming an ophthalmic device encapsulating the ophthalmic insert device is disclosed. In some embodiments, the encapsulating layer is paralene. In some embodiments, the encapsulating layer is forming a hydrogel around the lens insert.

In some embodiments, the first conductive trace includes a transparent electrode. In some other embodiments, the transparent electrode includes indium tin oxide. In some embodiments, the thin film transistor comprises an n-type organic semiconductor. In some embodiments, the thin film transistor comprises a p-type organic semiconductor. In some embodiments, the thin film transistor comprises an n-type organic semiconductor and a p-type organic semiconductor. In some embodiments, the n-type organic semiconductor layer comprises copper hexadecafluorophthalocyanine ($F_{15}CuPc$). In some embodiments, the p-type organic semiconductor layer comprises pentacene.

In some embodiments, a method of depositing an energization element upon the ophthalmic insert device in electrical communication with a first gate conductor is disclosed. In some embodiments, the energization element is an electrochemical cell. In some embodiments, electrochemical cell is a lithium ion cell.

In some embodiments, the ophthalmic lens insert may be formed in a number of manners to result in a three-dimensional shape upon which organic semiconductor transistors and other electrical devices may be formed. Non-limiting examples of electrical devices include resistors, capacitors, diodes, inductors, and similar such devices. Thereafter, energization elements may be formed in contact with or upon these organic semiconductor devices. In some embodiments, the energization elements may be formed by applying films that contain battery cell-related chemicals to electrical interconnections. In some other embodiments, the energizing elements may also be used in creating circuits of the organic semiconductor devices. In related embodiments, the application may be performed by printing processes that may apply mixtures of the chemicals by using needles or other application tools.

An ophthalmic lens may be formed by encapsulating a three-dimensionally formed ophthalmic insert in polymerized material. A method of forming the lens may include the polymerization of a reactive mixture between mold pieces where the ophthalmic insert is placed before polymerization. In some embodiments, numerous functional components or regions may be located within the ophthalmic insert. In some embodiments, the insert may contain at least one transistor that is formed from an organic semiconductor layer. Other common elements may include, but are not limiting to, conductive traces, energization elements, activation elements, and active ophthalmic devices. The active ophthalmic devices may be capable of dynamically changing the focal characteristics of the light that passes through the ophthalmic lens. A non-limiting example of a component capable of dynamically changing the focal characteristics may include a liquid meniscus lens element. Non-limiting examples of activation elements may include pressure sensitive switches, and magnetic field sensors. Non-limiting examples of magnetic field sensors may include Hall Effect sensors, photo detectors, sound detectors, and other devices capable of detecting electromagnetic signals, such as RF Signals.

In some embodiments, the organic semiconductor devices may be formed from n-type organic semiconductor layers. In other embodiments, the organic semiconductor devices may be formed from p-type organic semiconductor layers. Still other cases may contain devices of both p- and n-type organic semiconductor layers.

In some embodiments, the conductive traces may be formed from various metallic layers; including films of silver, gold, aluminum, and copper as a few examples. Other conductive traces may be formed of transparent materials such as, but not limiting to, indium tin oxide. In some embodiments, the energizing element may be located upon the conductive traces or connecting to the conductive traces. A non-limiting example of an energization element may be a battery. In some embodiments, the batteries may be formed from a solid-state processing, including, but not limiting to, various lithium battery processing. In some embodiments, batteries may be formed from wet-cell type formulations, such as but not limiting to, alkaline-type electrochemical cells.

In some embodiments, the ophthalmic lenses that are formed in these manners define novel types of ophthalmic devices. In some embodiments, the insert devices that are incorporated within the ophthalmic devices are novel. In some other embodiments, novel methods of producing ophthalmic devices that include organic semiconductor devices are described. Thin-film organic semiconductor devices may be formed from a patterned definition of electrodes, dielectrics, insulators, and layers of organic semiconductors. In some other embodiments, the resulting devices may be formed upon ophthalmic insert surfaces with a three-dimensional character. In some other embodiments, thin-film organic semiconductor devices may be formed into three-dimensional shapes after the formation of the organic semiconductor devices. In some embodiments, the formed circuits comprising organic semiconductor devices may also be conductively attached to three dimensional insert surfaces by various means including, but not limiting to, solders and conductive adhesives.

In some embodiments, the inserts which contain organic semiconductor devices may be further processed to form conductive traces and energization elements. Alternatively, in some other embodiments, conductive traces and energization elements may be formed prior to the inclusion of the organic semiconductor devices to three-dimensional inserts.

In some embodiments, various combinations of the elements may define novel embodiments. In some embodiments, energization elements with higher electrical potential may be formed from the series combination of individual electrochemical cells. The higher potential energization elements may provide energization to numerous activation elements including, but not limiting to, pressure sensitive contact switches. In addition, the higher potential energization elements may provide energization to the organic semiconductor circuits. In some embodiments, the novel combination of elements may define ophthalmic devices and the methods of forming them where the devices have simplified manufacturing processes due to the ability of organic semiconductors to be formed upon substrates like plastics at relatively low temperatures. Similarly, the nature of thin film transistors and other electrical devices based upon organic semiconductors, along with other processing aspects of the formation of inserts, may allow for the enablement of thinner ophthalmic devices.

DESCRIPTION OF THE DRAWINGS

FIG. 5 illustrates an exemplary process flow for the creation of complementary organic semiconductor devices consistent with later inclusion into ophthalmic devices.

DETAILED DESCRIPTION OF THE INVENTION

Figure 1:
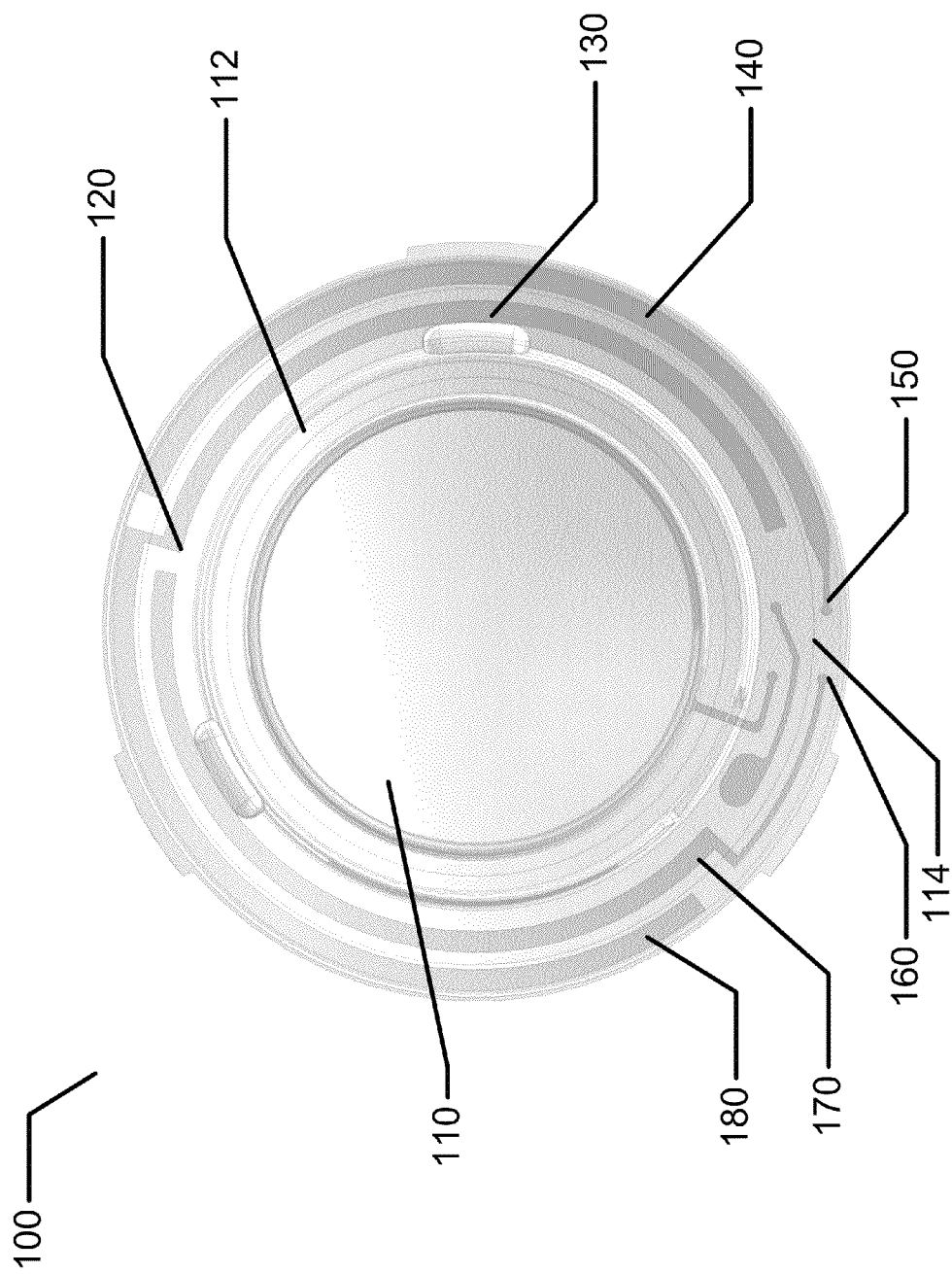
FIG. 1 illustrates an exemplary substrate with three-dimensional surfaces upon which organic semiconductor devices may be defined consistent with other related disclosures of the inventive entity.

The present invention relates to apparatus and methods for the formation of organic semiconductor devices upon ophthalmic insert structures. In some embodiments, the insert structure may have surfaces that have three-dimensional topology. In the following sections, detailed descriptions of embodiments of the invention will be given. The description of both preferred and alternative embodiments are exemplary embodiments only, and it is understood that to those skilled in the art that variations, modifications and alterations may be apparent. It is therefore to be understood that said exemplary embodiments do not limit the scope of the underlying invention.

GLOSSARY

In this description and claims directed to the presented invention, various terms may be used for which the following definitions will apply:

Encapsulate as used herein refers to creating a barrier to separate an entity, such as, for example, a Media Insert, from an environment adjacent to the entity.

Encapsulants: as used herein refers to a layer formed surrounding an entity, such as, for example, a Media Insert, that creates a barrier to separate the entity from an environment adjacent to the entity. For example, Encapsulants may be comprised of silicone hydrogels, such as Etafilcon, Galyfilcon, Narafilcon, and Senofilcon, or other hydrogel contact lens material. In some embodiments, an Encapsulant may be semipermeable to contain specified substances within the entity and preventing specified substances, such as, for example, water, from entering the entity.

Energized: as used herein refers to the state of being able to supply electrical current to or to have electrical energy stored within.

Energy: as used herein refers to the capacity of a physical system to do work. Many uses within this invention may relate to the said capacity being able to perform electrical actions in doing work.

Energy Source: as used herein refers to device or layer that is capable of supplying Energy or placing a logical or electrical device in an Energized state.

Energy Harvesters: as used herein refers to devices capable of extracting energy from the environment and converting it to electrical energy.

Functionalized: as used herein refers to making a layer or device able to perform a function including for example, energization, activation, or control.

Lens: refers to any ophthalmic device that resides in or on the eye. These devices may provide optical correction or may be cosmetic. For example, the term lens may refer to a contact lens, intraocular lens, overlay lens, ocular insert, optical insert or other similar devices through which vision is corrected or modified, or through which eye physiology is cosmetically enhanced (e.g., iris color) without impeding vision. In some embodiments, the preferred lenses of the invention are soft contact lenses that are made from silicone elastomers or hydrogels. Examples of hydrogels include, but are not limited to, silicone hydrogels, and fluorohydrogels.

Lens forming mixture or "Reactive Mixture" or "RMM" (Reactive Monomer Mixture): as used herein refers to a monomer or prepolymer material that may be cured and crosslinked or crosslinked to form an ophthalmic lens. Various embodiments may include, but are not limited to, lens forming mixtures with one or more additives such as: UV blockers, tints, photoinitiators or catalysts, and other additives one might desire in ophthalmic lenses such as, contact or intraocular lenses.

Lens Forming Surface: as used herein refers to a surface that is used to mold a lens. In some embodiments, such surface can have an optical quality surface finish. An optical quality surface finish may indicate that the surface is sufficiently formed and smooth so that a lens surface fashioned by the polymerization of a lens-forming material in contact with the molding surface is optically acceptable. Further, in some embodiments, the lens forming may have a geometry that is necessary to impart to the lens surface the desired optical characteristics, including without limitation, spherical, aspherical and cylinder power, wave front aberration correction, corneal topography correction, and combinations thereof.

Lithium Ion Cell: as used herein refers to an electrochemical cell where Lithium ions move through the cell to generate electrical energy. This electrochemical cell, typically called a battery, may be reenergized or recharged in its typical form.

Substrate insert: as used herein refers to a formable or rigid substrate capable of supporting an Energy Source within an ophthalmic lens. In some embodiments, the Substrate insert also supports one or more components.

Mold: as used herein refers to a rigid or semi-rigid object that may be used to form lenses from uncured formulations. Non-limiting examples of molds include two mold parts forming a front-curve mold part and a back-curve mold part.

Ophthalmic Lens Insert: as used herein refers to media that may be contained within or on an ophthalmic device, wherein the ophthalmic device may be worn by a human being.

Optical Zone: as used herein refers to an area of an ophthalmic lens through which a wearer of the ophthalmic lens sees.

Organic Semiconductor: as used herein refers to a semiconductor that is made from carbon-based materials.

PETG: as used herein refers to Polyethylene Terephtalate Glycol that is a clear amorphous thermoplastic that can be injection molded, sheet extruded, and colored during processing.

Power: as used herein refers to work done or energy transferred per unit of time.

Rechargeable or Re-energizable: as used herein refers to a capability of being restored to a state with higher capacity to do work. Many uses within this invention may relate to the capability of being restored with the ability to flow electrical current at a certain rate for certain, reestablished time period.

Reenergize or Recharge: as used herein refers to restore to a state with higher capacity to do work. Many uses within this invention may relate to restoring in a device the capability to flow electrical current at a certain rate for certain, reestablished period.

Released from a mold: as used herein means that a lens is either completely separated from the mold, or is only loosely attached so that it may be removed with mild agitation or pushed off with a swab.

Stacked: as used herein means to place at least two component layers in proximity to each other such that at least a portion of one surface of one of the layers contacts a first surface of a second layer. In some embodiments, a film, whether for adhesion or other functions, may reside between the two layers that are in contact with each other.

Stacked Integrated Component Devices (SIC-Devices): as used herein refers to a packaging product that is assembled from thin layers of substrates-which may contain electrical and electromechanical devices-into operative integrated devices by means of stacking at least a portion of each substrate layer upon each other. The substrate layers may include component devices of various types, materials, shapes, and sizes. Furthermore, the layers may be made of various device production technologies to fit and assume various contours, as it may be desired.

Referring now to FIG. 1, an ophthalmic lens is illustrated that includes one or more energization elements for inclusion of semiconductor devices. The methods and apparatus described herein relate to forming organic semiconductor devices within or on three-dimensionally formed substrates. The substrates may include electrical interconnects upon their respective surfaces. As illustrated, in some embodiments, an exemplary three-dimensional substrate 100 with electrical traces upon it is depicted. The example may represent a portion of an ophthalmic device or in other terminology may represent a portion of an insert device for an ophthalmic application. One such embodiment may include an ophthalmic device where an active focusing element is included. Such active focusing device may function while utilizing energy that may be stored in an energization element. The electrical traces upon the three dimensional substrate in FIG. 1 may provide a good substrate to form energization elements upon. Furthermore, discrete organic semiconductor devices or circuits formed from organic semiconductor devices may be connected to these electrical traces in various manners.

Referring back to FIG. 1, in some embodiments, in the ophthalmic device 100, the three dimensional substrate may include, as for example, a region 110 that is optically active. In some embodiments, if the ophthalmic device 110 is a focusing element, the active ophthalmic region 110 may represent a front surface of an insert device that contains the focusing element through which light passes into a user's eye. Outside of this region 110, there may typically be a peripheral region 112 of the ophthalmic device 100 that is not in a path optically relevant to a person wearing the ophthalmic device. In some embodiments, it may be appropriate to place components related to the active focusing function in such a peripheral region 112, although it is feasible—especially with very thin films and transparent electrodes—to place devices in the optically active region 110. In some embodiments, the transparent electrodes may be formed from material including, but not limiting to, indium tin oxide (ITO).

In some embodiments, in another aspect, various components may be electrically connected to each other by metal traces; some of these components may be or may contain organic semiconductor devices. Metal traces may also provide a useful function to support the incorporation of energizing elements 114 into the ophthalmic device 100.

Referring back to FIG. 1, in some embodiments, an energization element 114 may be a battery. For example, the battery may be a solid-state battery or a wet-cell battery. In either of these examples, there may be a minimum of at least two traces that are electrically conductive to provide for an electrical potential formed between the anode of the battery and a cathode of the battery. In the exemplary ophthalmic device 100 of FIG. 1, in some embodiments, a battery connection 114 may be defined in the region of an electrical trace 150. In some embodiments, the first energization element or battery 150 may be the anode connection and represent the (−) potential connection of an electrical trace 114 to the ophthalmic device 100.

Referring back to FIG. 1, in some embodiments, the second energization element, or battery 160 may be the cathode connection and represent the (+) potential connection of an electrical trace 114 to the ophthalmic device 100. In some embodiments, Organic semiconductor elements may be connected to anode 150 and cathode 160 connection points. In latter sections, some of these embodiments may be discussed in further detail. In one embodiment, an integrated circuit of organic semiconductor devices may be connected at anode 150 and at cathode 160 as well as other locations. In other embodiment types, the organic semiconductor devices may be formed directly upon the substrate surface of ophthalmic device 100 and either connect with anode 150 and cathode 160 or are integrally connected by using the same metallurgy for interconnections within the circuit devices themselves.

Referring back to FIG. 1, it may be observed that the electrical traces that are connected to anode 150 and cathode 160 are isolated traces 140 and 170 respectively that lay close to neighboring traces 130 and 180 respectively. The neighboring traces 130 and 180 may represent an opposite battery chemistry or electrode type when battery elements are produced upon these traces. Thus, a neighboring trace 130 may be connected to a chemical layer that may make it function as a cathode 160 of a battery cell between the neighboring trace 130 and the isolated trace 140.

In FIG. 1, the neighboring traces 130 and 180 may be observed to connect to each other through the trace region 120. The trace region 120 may, in some embodiments, be partially covered or not covered by any chemical layers. Therefore, the trace region 120 functions for the purpose of electrical interconnection. It may be apparent that in this example, there may be two pairs of electrical cells configured as batteries and that the nature of the layout and design connects these two batteries in a series connection. The total electrical performance across energization elements 150 and 160 may be considered a combination of two battery cells.

In embodiments that incorporate organic semiconductor devices, the energization voltage requirements may be in the 10's of volts and accordingly there may be numerous trace regions 120 that are formed to allow the energization elements 150 and 160 to define a higher total energization voltage.

Figure 2:
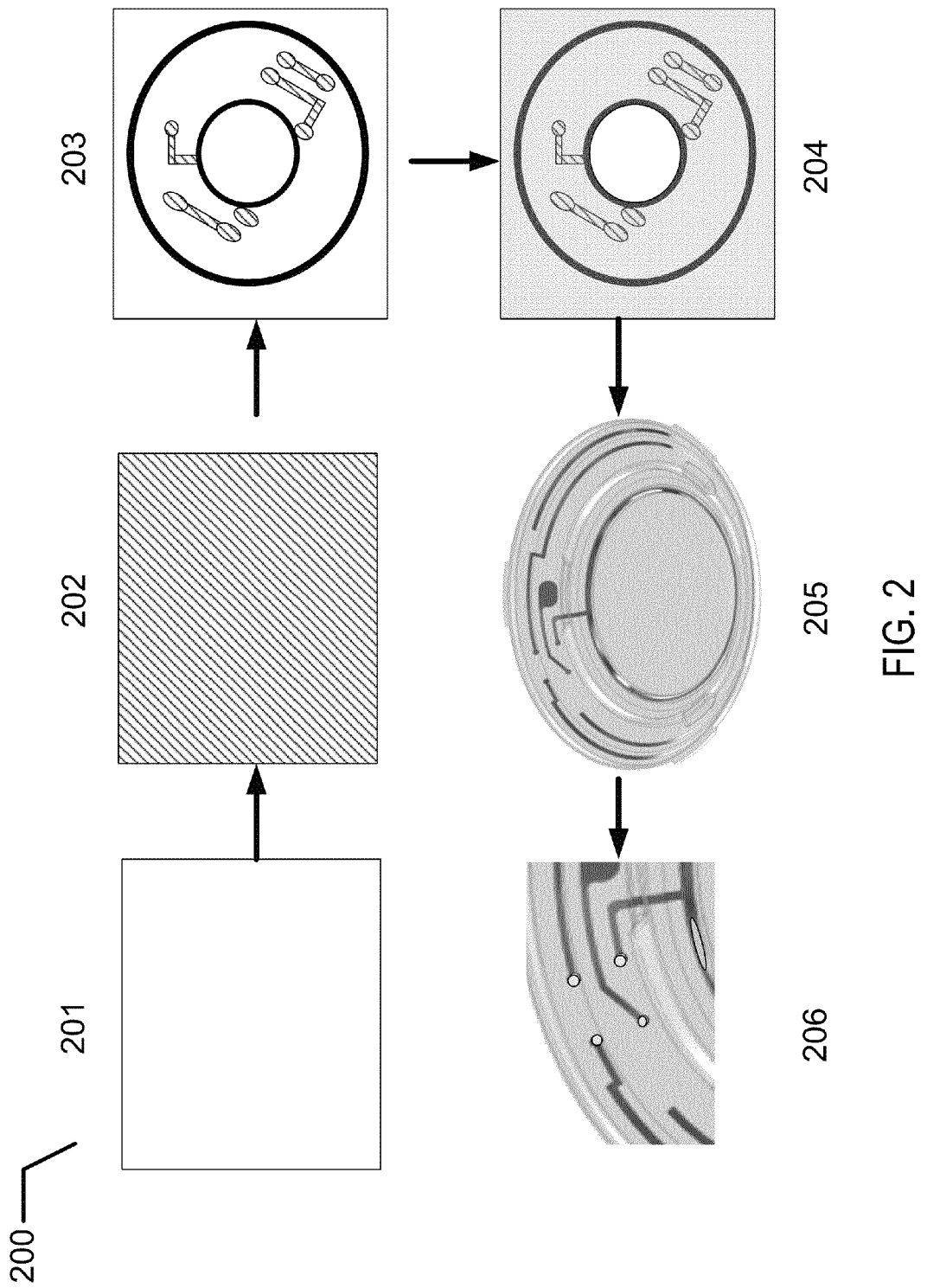
FIG. 2 illustrates an exemplary flow for forming three-dimensional surfaces that may be consistent with the formation of organic semiconductor devices.

An alternative set of embodiments may be described in reference to FIG. 2. In these alternative embodiments, a set of conductive features 200 are formed which, after processing, become interconnects on a three dimensional surface are formed while base materials are still kept in a planar shape. Proceeding to step 201, a base substrate, which in some embodiments may be consistent with forming a part of an ophthalmic lens or lens insert, is formed. Non-limiting examples of the base substrate material may include PETG. In some embodiments, if the base substrate is formed from a conductive material, its surface may be coated with an insulator material to remain consistent with formation of interconnects on the surface.

In some embodiments, organic semiconductor processing may occur onto this substrate surface. In these cases, the processing steps, which will be described in later sections, may have already been performed upon the substrate and therefore the substrate of 201 may actually include organic semiconductor devices upon its surface. In some embodiments, subsequent processing steps of FIG. 2 may be performed upon these device regions and the flat substrates. In other embodiments, the organic semiconductor devices may be formed in a similar manner to the process of FIG. 2, but in a parallel processing manner. Referring back to FIG. 2, the substrate base is further processed at step 202. In some embodiments, a conductive film is applied upon the base substrate. The conductive film may comprise alternatives consistent with the art herein defined for this embodiment and the others to be discussed. In some embodiments, the film may be formed of a malleable conductive material and of a sufficient thickness to avoid mechanical failure during the later forming processes.

The conductive film may be deformed as the flat substrate base is formed into a three dimensional substrate. In some embodiments, the film may be comprised of a gold film.

Referring back to FIG. 2, at step 203, the conductive film may be patterned to form a desired shape after the flat pieces are formed into three-dimensional shapes. The depicted shapes are exemplary set of shapes that would form the three-dimensional desired result. There may be numerous manners to pattern the conductive layer, including, but not liming to a gold conductive layer. A non-limiting example of the patterning step 203 may include photolithography with chemical etching. Alternatively, laser ablation may be used in the manners previously describe to create the appropriate shaped features. In some embodiments, the imaged conductor patterns may have been deposited through a screen directly into the patterned shape.

Referring back to FIG. 2, in some embodiments, at step 204, the stack of the base substrate with overlying conductive features may be encapsulated in an overlying material. In some embodiments, a thermoforming material, such as, but not limiting to, PETG may provide an exemplary film that could be used in this manner. In some embodiments, encapsulation of the formed features may result in a desirable stability of the features. In some other embodiments, a stack of films may be deformed during thermoforming processes to create the desirable three-dimensional shapes. In some embodiments, as part of step 204, a first planar thermoforming process may occur to seal the overlying insulative material to the underlying substrate base and to the defined features in the conductive film. Additionally, a cutout for the central optic zone region is illustrated by the non-shaded central circular region since the central optic region may perform better without a composite film.

Referring back to FIG. 2, at step 205, the stack of base material, formed conductive features, overlying encapsulating layers, and insulating layers may be subjected to a thermoforming process to result in a three-dimensional shape. In some embodiments, the shape may incorporate the electrical interconnects resulting from the thermoforming process. In some embodiments where the processing at step 204 included an overlying insulating layer, vias may be formed into the insulating material. At step 206, the three-dimensional shape with incorporated electrical interconnects is processed to create electrical conductive vias and openings at appropriate locations. There may be numerous manners to create these vias and openings; however, in a non-limiting example, laser ablation processing may be used to create precise openings by ablating the top insulator layer and exposing an underlying conductive film area. The resulting three-dimensional surface with electrical interconnects may be significantly similar to that produced in other manners discussed herein.

Figure 3:
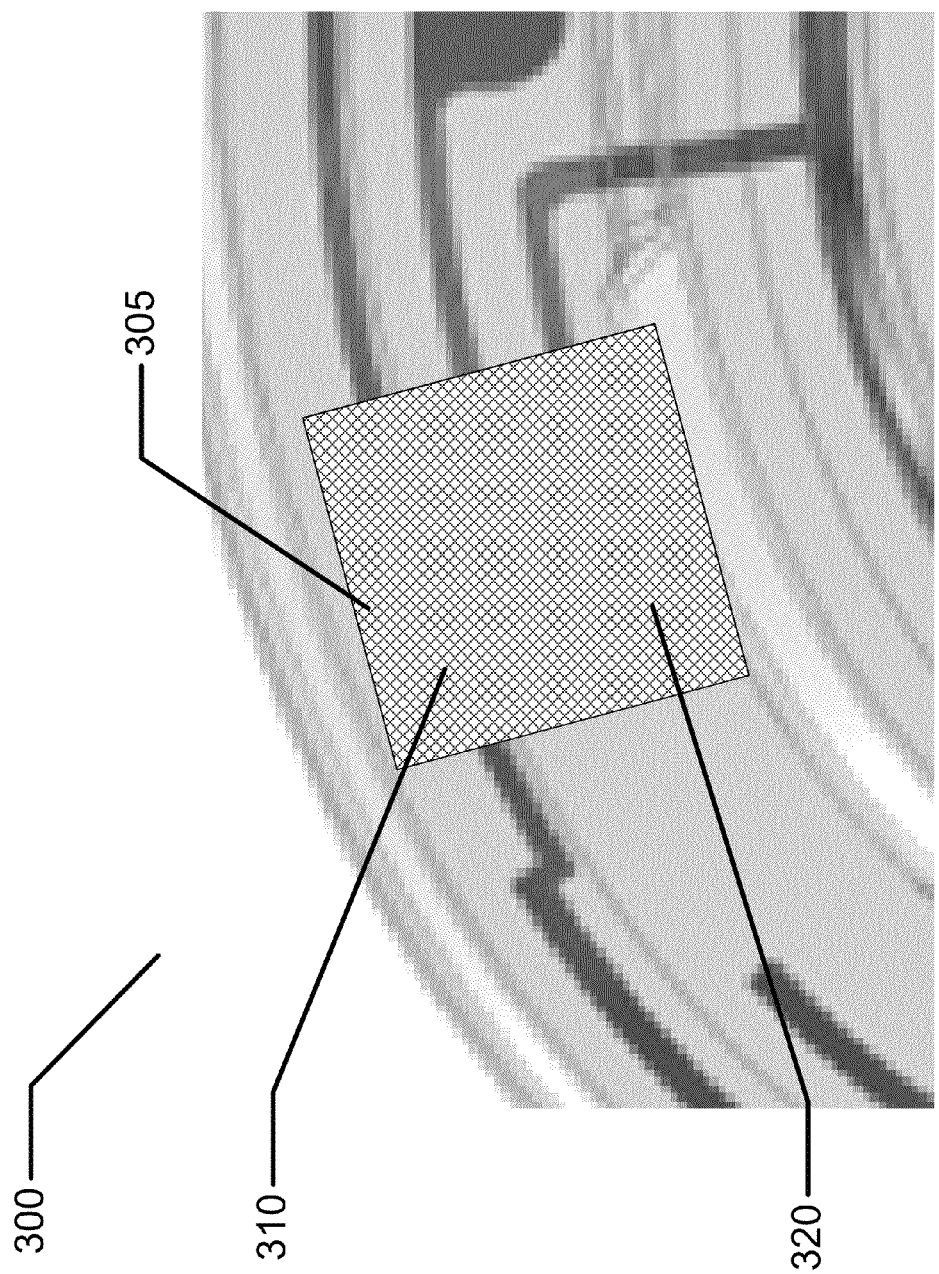
FIG. 3 illustrates an integrated circuit device that is connected to a three dimensionally formed insert device with conductive traces in at least two electrically conductive locations.

Electrically Connecting Organic Semiconductor Devices Upon Three Dimensionally Formed or Formable Insert Substrates Referring now to FIG. 3, electrically connecting Organic Semiconductor devices upon three dimensionally formed or formable insert substrates are illustrates. In some embodiments, an exemplary close up of a portion of the three dimensionally formed insert component 300 is depicted. The location indicated by region 305, may represent either an attached integrated circuit device that may contain organic semiconductor devices, or it may represent the region of the insert surface upon which organic semiconductor devices have already been formed or may be formed in subsequent processing.

In some embodiments, the regions 310 and 320 may represent locations where the larger interconnection features of the insert device make electrical connection to components in the circuit region. In the exemplary illustration in FIG. 3, the organic semiconductor components may be cut out or diced from a substrate and subsequently connected to the insert. The depiction in FIG. 3, therefore, may represent a flip-chip orientation in regions 310 and 320, but there may be interconnect features such as, but not limiting to, flowable solder balls, or conductive epoxy connections under the chip surface.

In either of the embodiment types, the nature of the connection schemes may ensure that organic semiconductor devices in the circuit region 305 are connected through interconnect traces to other elements. These other elements may include, but are not limited to, energization elements, sensors, active optical elements, other integrated circuit designs, medicament pumps, and medicament dispersal devices.

In some embodiments, organic semiconductor transistors may be formed on Ophthalmic Insert surfaces. There may be numerous methods of incorporating organic semiconductor devices into ophthalmic insert devices. In some embodiments, there may be numerous methods of forming the organic semiconductor devices to be incorporated. In some other embodiments, organic semiconductor devices are formed based on field-effect semiconducting device structures. Non-limiting examples of these devices include designs that have a gate electrode lying under the semiconductive layer, wherein additional embodiments include a gate electrode above the semiconductor layer, or have the gate electrode at a semiconductor layers.

Figure 4:
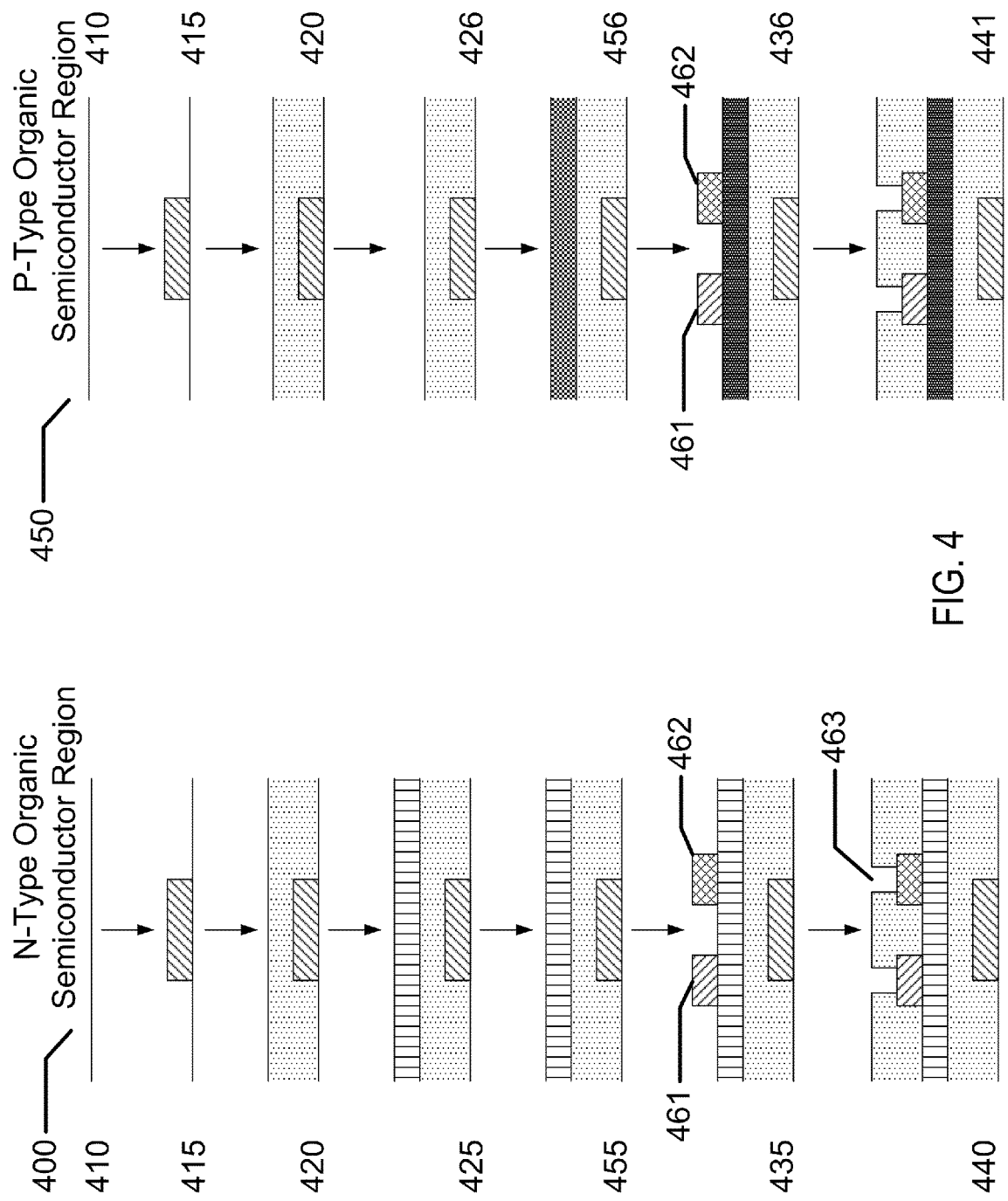
FIG. 4 illustrates an exemplary set of processing flow steps for the formation of complementary n and p-type organic semiconductor devices that may be useful for the inclusion into ophthalmic devices.

Proceeding to FIG. 4, parallel processing flows 400 and 450 are illustrated that produce complementary p- and n-type organic semiconductor devices. At step 410 for each type of device the substrate may be a flat or planar upon which the devices may be formed. Next, at step 415, a metallic or conductive material is deposited to form the gate electrode in this "bottom gate" electrode type of processing flow. There may be numerous means to form the gate electrode including screened deposition from a sputtered or evaporated source. Other methods may include blanket deposition followed by patterned etching processes. Any method of forming isolated conductive gate structures may be consistent with the art herein.

In the following step 420, a gate dielectric layer is deposited to cover and surround the gate electrode. An effective method for this deposition may be to spin on the dielectric from a liquid precursor followed by curing. In other embodiments, the dielectric may be deposited by vapor deposition. In some embodiments, the dielectric may be subsequently planarized by a technique such as, but not limiting to, chemical mechanical polishing.

Referring back to FIG. 4, at step 425, the n-type organic semiconductor layer may be deposited upon the dielectric layer. This deposition may be regionally controlled by masked deposition of vapor phase forms of the organic semiconductor. In other embodiments, a blanket film may be applied followed by a patterned removal process. In some other embodiments, at 426, the n-type organic semiconductor layer may not be present. In some examples of ambipolar devices, the n-type organic semiconductor film may be present in the p-type devices and then later covered by p-type organic semiconductor material (not shown). Some materials for this layer may include N, N'-bis(n-octyl)-dicyanoperylene-3,4,9,10-bis(dicarboximide) otherwise called (PDI-8CN2); carbonyl functionalized ($\alpha,\omega$-diperfluorohexyl-4T) otherwise called (DFHCO-4T) and copper hexadecafluorophthalocyanine otherwise called ($F_{15}CuPc$) as a few non-limiting exemplary options.

Referring back to FIG. 4, at step 456, the p-type organic semiconductor layer may be deposited upon the dielectric layer. This deposition may be regionally controlled by masked deposition of vapor phase forms of the organic semiconductor. In other embodiments, a blanket film may be applied followed by a patterned removal process. At step 455, it may be observed, in some embodiments, that the p-type organic semiconductor layer is not present. Some materials for this layer may include pentacene, tetracene, rubrene, and regioregular poly(3-hexylthiophene) (P3HT) as a few non-limiting exemplary options. Specific examples have been discussed but the many materials that may make acceptable n- and p-type organic TFT devices may be consistent within the scope of the art herein.

Referring back to FIG. 4, source and drain electrodes 461 and 462 respectively are next placed on the formative organic semiconductor transistor device. As depicted in FIG. 4, two separate steps are defined as step 435 and step 436. In many embodiments, these steps will occur simultaneously and the distinction of the step number is just to highlight that the steps are occurring on different layers. There may be numerous means to form the source/drain electrodes including screened deposition from a sputtered or evaporated source. Other methods may include blanket deposition followed by patterned etching processes. Any method of forming isolated conductive electrode structures may be consistent with the art herein.

Referring back to FIG. 4, proceeding to steps 440 and 441, insulator may be placed to encapsulate the source and drain electrodes and the entire devices themselves. An effective method for this deposition may be to spin on the dielectric from a liquid precursor followed by curing. In other embodiments, the dielectric may be deposited by vapor deposition and in some cases subsequently planarized by a technique such as, but not limited to, chemical mechanical polishing as a non-limiting example. Following the deposition of the insulator layer, contact openings 463, may be formed. Amongst the various processing steps that could perform these contact openings may be laser ablation processing or lithography-imaged subtractive etching processes as non-limiting examples.

Referring now to FIG. 5, in some embodiments, the process flow 500 is summarized in textual form for the method and manner of forming organic semiconductor devices. At step 501, a flat substrate is cleaned in preparation for processing into an organic semiconductor device. It may be possible to process any three-dimensionally formed surfaces in the manners discussed, but for exemplary purposes, a flat substrate is described. Next at step 502, the gate metal features are deposited and defined spatially. The exemplary flow is for a type of gate under device structure. In some embodiments, the numerous TFT architectures known in the art may be consistent with the scope of the art herein. Proceeding further to step 503, a dielectric film layer is deposited over and around the gate electrode. In a preferred embodiment, the dielectric layer may be approximately parallel and flat above the gate dielectric after this processing. At steps 504 and 505 the n-type and p-type organic semiconductor layers are deposited into selected regions. There may be numerous manners to deposit these selected regional layers including, but not limiting to, masked depositions and blanket depositions followed by subtractive etches. Further, in some embodiments, the order of the two regions may be reversed. In some embodiments, both n- and p-type organic semiconductor devices may be formed. This may be desirable in circuit flexibility, but may also allow for the formation of various non-transistor devices such as formation of a diode by the combination of n- and p-type layers. At step 506, the source and drain electrodes are formed. As previously stated, this example is for a gate under device type and may represent an embodiment where the source and drain electrodes are deposited over a roughly planar semiconductor region. However, the diversity of TFT architectures may be consistent with the art herein. Next, at step 507, in some embodiments, the device and electrodes may be surrounded by an encapsulating and insulating layer. In some embodiments, this layer will be formed or processed to yield a planar top surface. At the final step depicted in FIG. 5, step 508, the contact holes in the dielectric insulating layers are formed, at least partially, above regions where the conductive electrodes are located. In some embodiments, the external electrical contact may be made to the formed devices. It may be obvious to one skilled in the art that the exemplary process flow may result in numerous connected organic semiconductor transistors to form functional circuits. As well, other devices than transistors, including diodes, resistors, and varactors may be formed.

Figure 6:
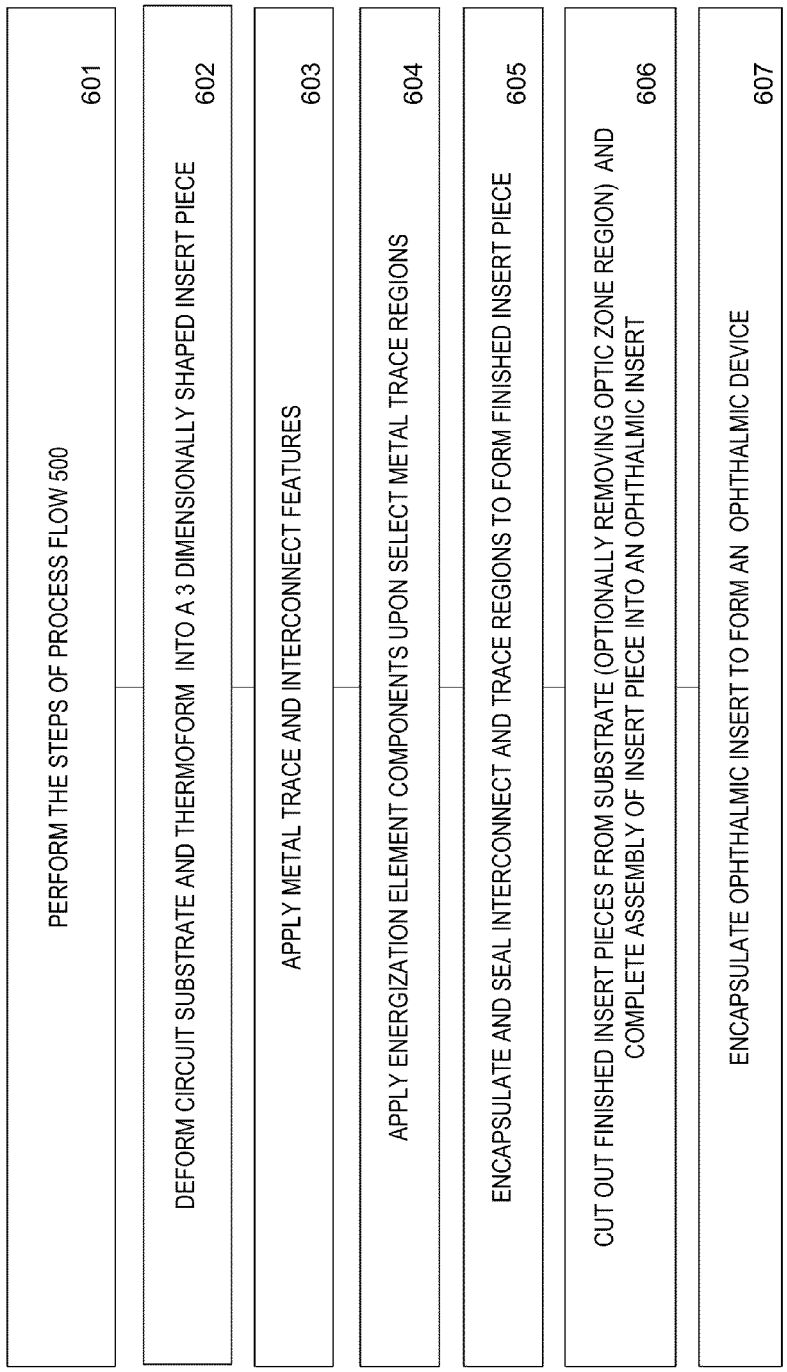
FIG. 6 illustrates an exemplary methodology for the further processing of the process flow referenced in exemplary fashion in FIG. 5 into an ophthalmic device.

Referring to FIG. 6, an exemplary process flow 600 to further process an ophthalmic device utilizing the planar processing depicted in process 500 is illustrated. At step 601, the further processing of process 500 depicted in FIG. 5, in part or full, may proceed. After that, the resulting substrate, organic semiconductor devices, conductive interconnections and any other formed devices on the substrate may be further processed at step 602. In some embodiments, at step 602, the substrate and devices may be deformed into a three-dimensionally shaped piece. In some embodiments, the deformation may involve thermoforming of the substrate in some examples, or may involve folding of the substrate in other embodiments.

Referring back to FIG. 6, at step 603, the resulting three-dimensionally shaped piece may have additional metal traces deposited upon it. In some embodiments, these metal traces may intersect with the conductive layer via openings formed during processing of the thin film organic semiconductor device. In some embodiments, the energization devices may not have been already placed upon the flat substrate, although such a placement may be possible within the state of the art. At step 604, the energization elements may be applied by various means including, for example, the printing of anodes, cathodes, and electrolyte regions.

Next, at step 605, in some embodiments, the devices may be encapsulated and sealed. There may be numerous manners to perform the encapsulation, such as, for example, the vapor phase deposition of parylene with screening apparatus to allow certain regions to remain unsealed or unencapsulated. In some embodiments, the resulting devices may next be singulated or cut out at step 606. In some embodiments, the central region of the formed insert piece—that may reside in the optic zone—may remain for various functional purposes, including, but not limiting to, forming the front optic surface for a meniscus based lens element. In other embodiments, the central optic zone may be removed to form an annular type ophthalmic insert piece. In some embodiments, continuing in this step 606, the formed ophthalmic insert piece may be subsequently processed to complete assembly into an ophthalmic insert.

Continuing with Fig., at step 607, in some embodiments, an ophthalmic device is formed. There may be numerous manners to form an ophthalmic device utilizing the ophthalmic insert of step 606. In some embodiments, this may involve placing the ophthalmic device into a front curved mold piece with a small amount of reactive mixture. By fixing the reactive mixture, the insert piece may be held to the mold piece in an appropriate location. Subsequently, in some embodiments, the front and back curve mold pieces may be utilized to mold an appropriate shape and optical quality to a produced ophthalmic lens device. In some other embodiments, the material that is formed in the molding step that encapsulates the insert may include hydrogel-forming materials.

Figure 7:
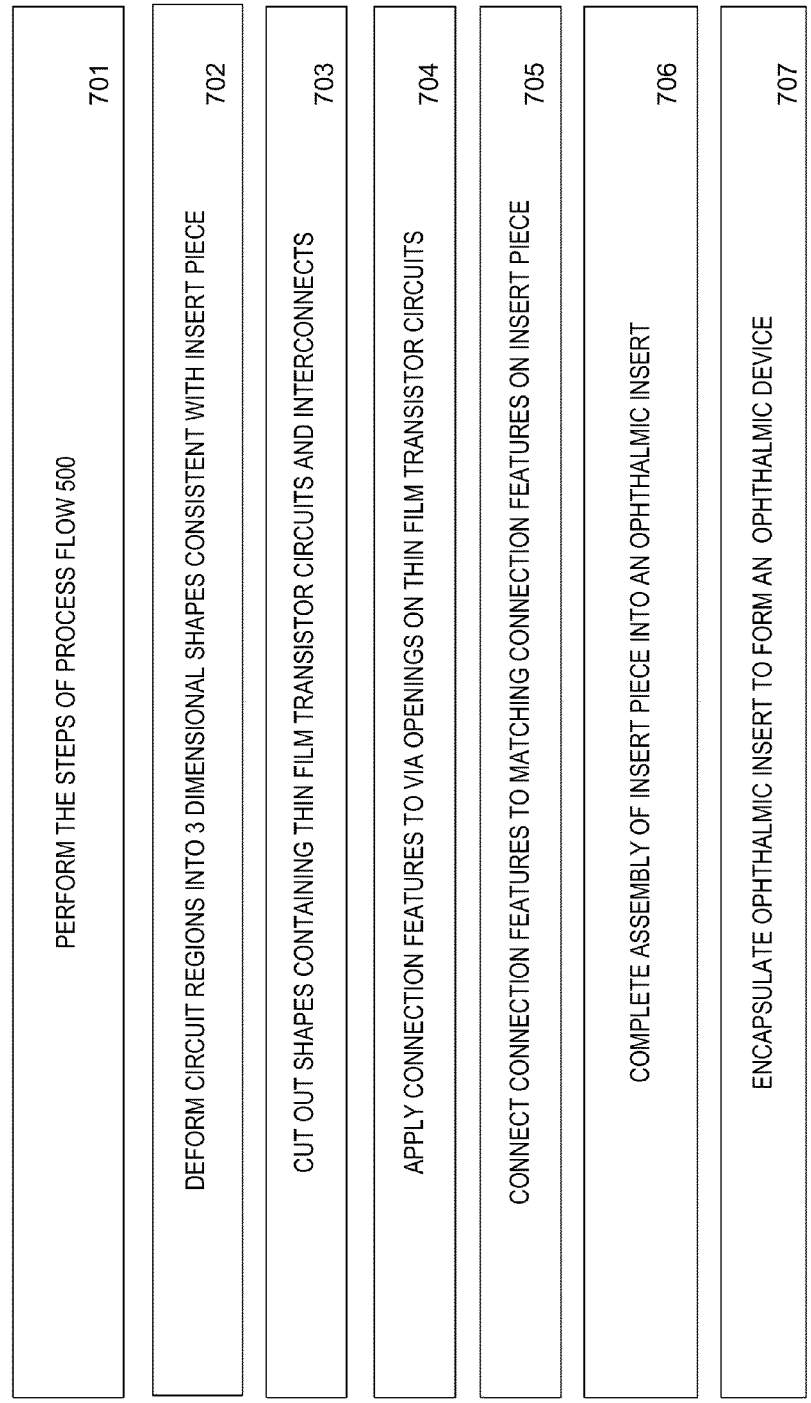
FIG. 7 illustrates an alternative exemplary methodology for the further processing of the process flow referenced in exemplary fashion in FIG. 5 into an ophthalmic device.

Referring now to FIG. 7, in some embodiments, an alternative method 700 to form ophthalmic devices comprising organic semiconductor devices is described. At step 701, further processing of process 500 may proceed, in part or full. In some other embodiments, the resulting substrate, organic semiconductor devices, conductive interconnections, and any other formed devices on the substrate may be further processed at step 702. In some embodiments, at step 702, the substrate and devices may be deformed into a three-dimensionally shaped piece. The deformation may involve thermoforming of the substrate in some examples. In other embodiments, the deformation may involve folding of the substrate based on thermoforming or adhesive bonding to keep the piece in its three-dimensional shape.

Referring back to FIG. 7, in some embodiments at step 703, the three-dimensional shape may be cut into segments containing a complete copy of the circuit for the ophthalmic device. Next, at step 704, in some embodiments connection features may be applied to the conductive layer via openings formed during the processing of the thin film organic semiconductor device. In some embodiments, these connection features may include solder bumps of various kinds. In other embodiments, the connection features may include conductive epoxy. In either of these embodiment types, at step 705, the sectioned circuit piece may be connected to a three-dimensionally formed insert piece where the connection features may be used in conjunction with other sealants and encapsulants to attach the segmented circuit piece to the ophthalmic insert piece. In some embodiments, at step 706, the resulting insert piece with the attached organic semiconductor may be finished into a complete ophthalmic insert.

Continuing with FIG. 7, in some embodiments at step 707, an ophthalmic device is formed. There may be numerous manners to form an ophthalmic device utilizing the ophthalmic insert of step 706. In some embodiments, this may involve placing the ophthalmic device into the front curved mold piece with a small amount of reactive mixture. In some embodiments, by fixing the reactive mixture, the insert piece may be held to the mold piece in an appropriate location. Subsequently, in some embodiments, front and back curve mold pieces may be utilized to mold an appropriate shape and optical quality into a produced ophthalmic lens device. In some embodiments, the molding material that encapsulates the insert may include hydrogel-forming materials.

Figure 8:
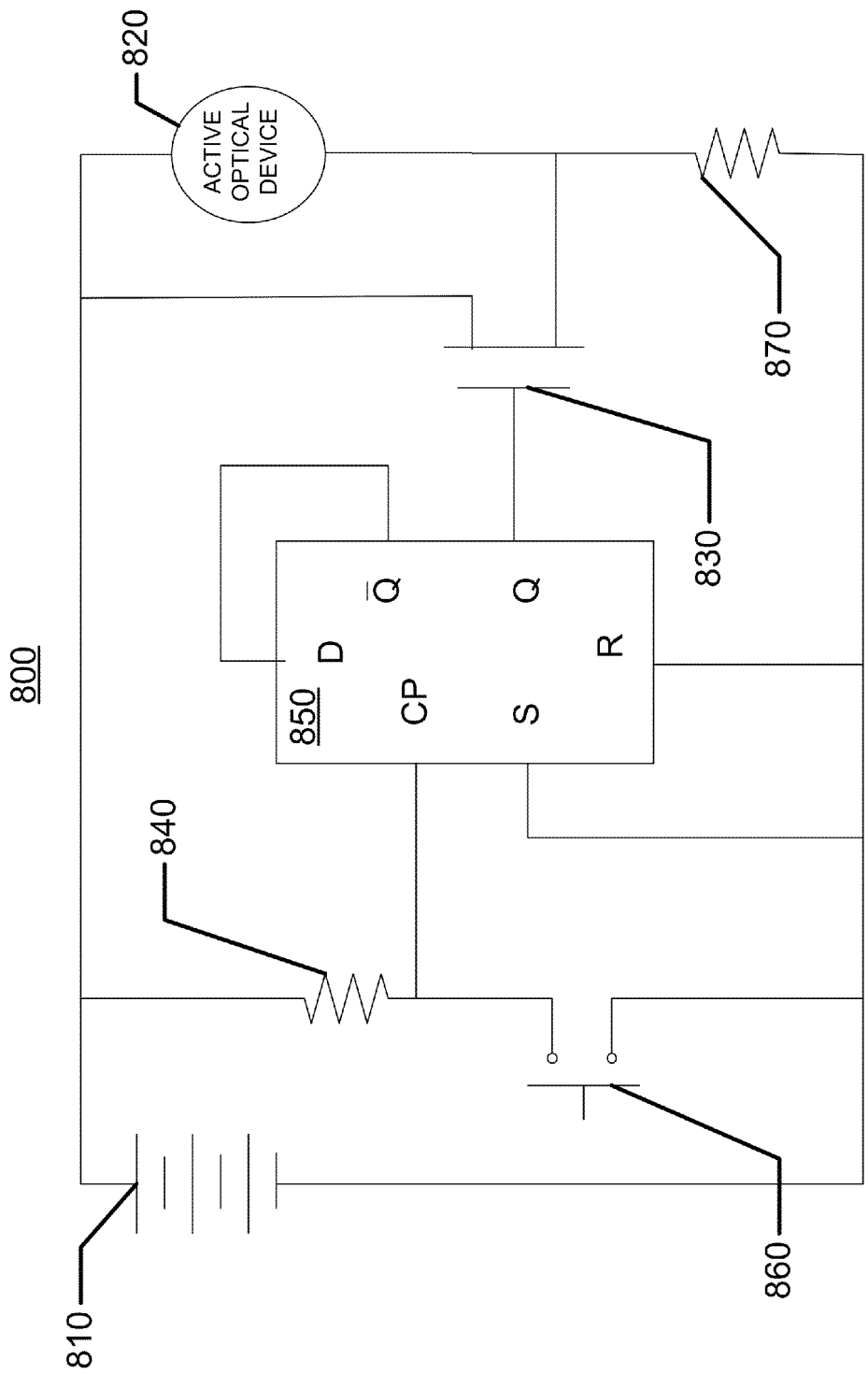
FIG. 8 illustrates an exemplary electronic circuit function utilizing organic semiconductors included into an ophthalmic device.

In some embodiments, the methods and apparatus mentioned in the prior sections may create various ophthalmic devices. Referring to FIG. 8, an exemplary electronic circuit 800 is described, which is consistent with the implementation of an ophthalmic device with an energization element. In some embodiments, the electronic circuit 800 responds to a mechanical switch as an activation device and applies electrical potential across an active ophthalmic device including a meniscus based focusing element, when the electronic circuit 800 is activated.

Referring back to FIG. 8, in some embodiments, an energization element 810 is depicted. In some embodiments, the energization element 810 may be comprised of various and numerous battery cells connected in a series manner, since the electronic circuit 800 may contain organic semiconductor transistors. As an example, in some embodiments, adequate cells may be connected to generate an electrical potential in the energization element of approximately 20 Volts. In other embodiments, a variety of a number of cells may be connected together to generate energization potentials ranging from approximately 10 Volts to 100 Volts.

Continuing with FIG. 8, in some embodiments, the energization element 810 may apply its potential across an active ophthalmic element 820. The active ophthalmic element 820 may be a meniscus lens-based device that responds by changing the shape of a meniscus based on the application of potential across two immiscible fluids. In some embodiments, the meniscus lens-based device functions essentially as an extremely high impedance capacitor from an electrical perspective. Therefore, the energization element 810 may initially charge the active ophthalmic element 820 through a first resistive element 870. When the potential fully charges the capacitive element, the energization element 810 will thereafter will not have a large dissipative load on it. In some other embodiments, a start up circuitry may be defined to further ensure that the energization element is not discharged.

In some embodiments, referring back to FIG. 8, the electronic circuit 800 may further include a "D-FlipFlop" circuit 850 based on a circuit using the complementary n- and p-type organic semiconductor transistors. In some embodiments, the D-FlipFlop circuit 850, may have its D and Q outputs connected together, as well as the Set (S) and Reset (R) being connected to ground. In some other embodiments, the output of Q will then flip from one state to the next every time there is a voltage level change at the Clock (CP) input. That input will be set by the energization source 810 through a second resistive element 840. In some embodiments, when an external switch 860 is activated as may be the case when a user exerts pressure onto a pressure-sensitive switch, the potential at CP is brought close to ground, and this level change may toggle the state of the D-FlipFlop 850. In some other embodiments, when the level changes at Q, a transistor 830 connected thereto may be "Turned-On" and conduct across the active optical device effectively shorting the device and allowing the state of the active optical state to be changed. There may be numerous manners to activate and control the status of the exemplary circuit embodiment.

Figure 9:
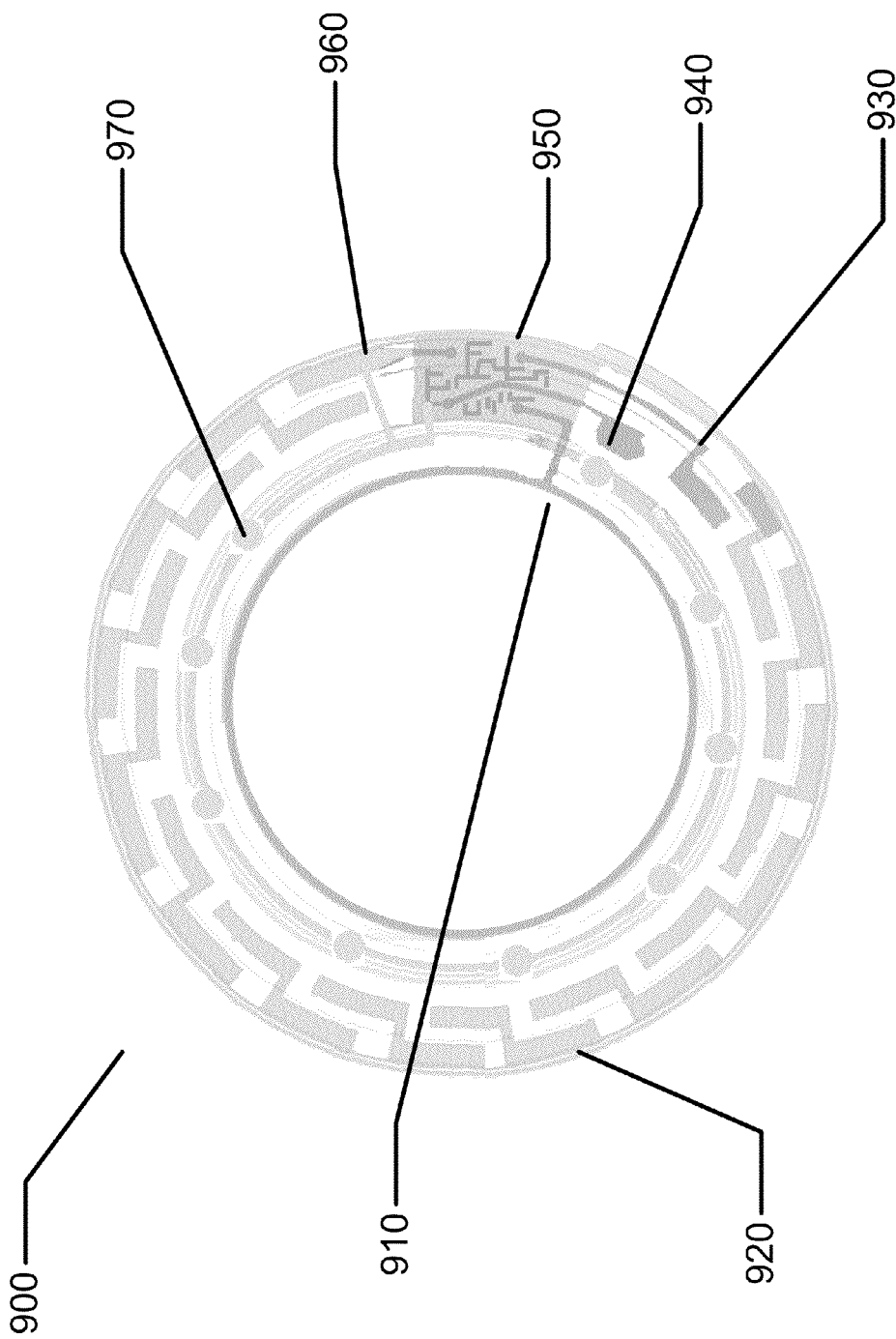
FIG. 9 illustrates a representation of an insert device that includes the circuit elements of FIG. 8.

Proceeding to FIG. 9, in some embodiments, a physical representation for an insert component piece 900, which is consistent with the embodiments of FIG. 8, is presented. In some embodiments, a first connection 910 for the meniscus lens device may be found. As mentioned, there may be numerous energization cells 920 that are connected in series in order to generate the necessary potentials required for operation of organic semiconductor-based circuits. In some embodiments, the combination of energizing cells 920 may define an energization element of roughly 20 volts. In some other embodiments, the energization element 920 may comprise contact points 930 and 940.

In some embodiments, the D-Type FlipFlop 950 may be found in the insert component piece 900. In some embodiments, the D-Type FlipFlop 950 may contain both the n- and p-type organic semiconductor transistors. Furthermore, the resistive elements may be defined in the D-Type FlipFlop 950 as well (not shown). In some embodiments, a second contact 960 that defines the alternative connection point for the meniscus lens may be present. In some other embodiments, a pressure sensitive switch 970 may be formed from spaced metallic traces that upon deflection by pressure, completes a contact between the two sides.

Specific examples have been described to illustrate aspects of inventive art relating to the formation, methods of formation, and apparatus of formation that may be useful to form energization elements upon electrical interconnects on three dimensional surfaces. These examples are for said illustration and are not intended to limit the scope in any manner. Accordingly, the description is intended to embrace all embodiments that may be apparent to those skilled in the art.

The invention claimed is:

1. A method of forming an ophthalmic device comprising:
preparing a flat substrate;
depositing gate metal features on predetermined areas on the flat substrate;
depositing a dielectric film layer over and around the gate metal features;

depositing organic semiconductor layers onto selective regions;

forming source and drain electrodes to create a thin film organic semiconductor device on the flat substrate;

deforming the flat substrate with the thin film organic semiconductor device into a three dimensionally shaped ophthalmic insert;

forming at least one first conductive trace on the three dimensionally shaped ophthalmic insert;

forming an encapsulating layer around the three dimensionally shaped ophthalmic insert; and forming an ophthalmic device encapsulating the three dimensionally shaped ophthalmic insert.

2. The method of claim 1, wherein the encapsulating layer is paralene.

3. The method of claim 2, wherein the encapsulating layer is forming a hydrogel around the lens insert.

4. The method of claim 1, wherein the first conductive trace comprises a transparent electrode.

5. The method of claim 4, wherein the transparent electrode comprises indium tin oxide.

6. The method of claim 1, wherein the thin film transistor comprises an n-type organic semiconductor.

7. The method of claim 1, wherein the thin film transistor comprises a p-type organic semiconductor.

8. The method of claim 1, wherein the thin film transistor comprises an n-type organic semiconductor and a p-type organic semiconductor.

9. The method of claim 6, wherein the n-type organic semiconductor layer comprises copper hexadecafluorophthalocyanine ($F_{15}CuPc$).

10. The method of claim 7, wherein the p-type organic semiconductor layer comprises pentacene.

11. The method of claim 1 additionally comprising:

depositing an energization element upon the ophthalmic insert device in electrical communication with a first gate conductor.

12. The method of claim 11 wherein:

the energization element is an electrochemical cell.

13. The method of claim 12 wherein:

The electrochemical cell is a lithium ion cell.

* * * * *